(12) United States Patent
Hasemann

(10) Patent No.: US 6,302,923 B1
(45) Date of Patent: Oct. 16, 2001

(54) TRIPHENDIOXAZINE COMPOUNDS

(75) Inventor: Ludwig Hasemann, Müllheim-Niederweiler (DE)

(73) Assignee: Clariant Finance (BVI) Limited, Tortala (VG)

( * ) Notice: Subject to any disclaimer, the term of this patent is extended or adjusted under 35 U.S.C. 154(b) by 0 days.

(21) Appl. No.: 09/574,331

(22) Filed: May 19, 2000

(30) Foreign Application Priority Data

May 21, 1999 (GB) .................................................. 9911719

(51) Int. Cl.[7] .............................. D06P 5/00; C09D 13/00; C07D 498/00
(52) U.S. Cl. .......................... 8/445; 8/918; 8/919; 8/924; 106/31.47; 544/75; 544/76; 544/77
(58) Field of Search .................... 544/76, 77; 106/31.47; 8/445, 918, 919, 924

(56) References Cited

U.S. PATENT DOCUMENTS

| | | | |
|---|---|---|---|
| 4,568,742 | 2/1986 | Harms et al. | 544/76 |
| 4,780,107 | 10/1988 | Sawamoto et al. | 8/657 |
| 5,068,327 | 11/1991 | Miyamoto et al. | 544/76 |
| 5,272,267 | 12/1993 | Miyamoto et al. | 544/76 |
| 5,438,137 | 8/1995 | Miyamoto et al. | 544/76 |
| 5,486,607 | 1/1996 | Miyamoto et al. | 544/76 |
| 5,696,258 | 12/1997 | Schumacher et al. | 544/76 |
| 5,944,854 | 8/1999 | Schumacher et al. | 8/549 |

FOREIGN PATENT DOCUMENTS

| | | | |
|---|---|---|---|
| 3341886 | * | 5/1985 | (DE) . |
| 773264 | * | 5/1997 | (EP) . |
| 275022 | * | 7/1998 | (EP) . |
| 08073789 | * | 3/1996 | (JP) . |
| 9954334 | * | 5/1997 | (WO) . |

OTHER PUBLICATIONS

PCT Search Report.
Derwent Patent Family Abstract for JP 08073789.

* cited by examiner

Primary Examiner—Mukund J. Shah
Assistant Examiner—Sudhaker B. Patel
(74) Attorney, Agent, or Firm—Scott E. Hanf

(57) ABSTRACT

Compounds of formula (I)

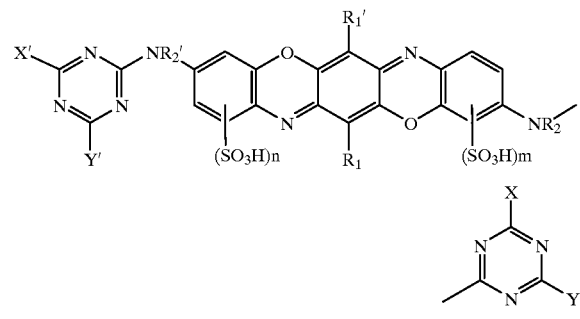

with the meanings of $R_1$, $R_1'$, $R_2$, $R_2'$, X, X', Y, Y', m and n as given in claim 1 can be used as paper dyes or direct dyes or for the preparation of ink-jet inks.

14 Claims, No Drawings

TRIPHENDIOXAZINE COMPOUNDS

The invention relates to new triphendioxazine compounds, to a process for producing the new triphendioxazine compounds and to their use as direct dyestuffs.

SUMMARY OF THE INVENTION

According to the invention compounds of formula (I)

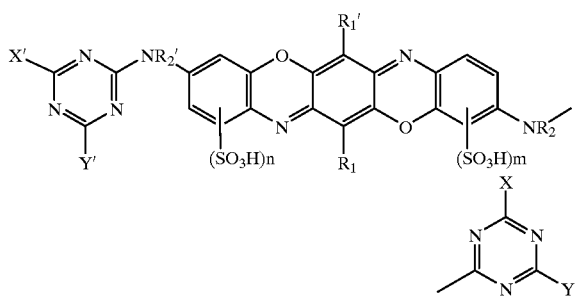

(I)

wherein

DESCRIPTION OF PREFERRED EMBODIMENTS $R_1$ and $R_1'$ independently from each other are hydrogen or halogen, $R_2$ and $R_2'$ independently from each other are hydrogen or $C_{1-4}$-alkyl, X and X' independently from each other are optionally substituted aliphatic, aromatic, cycloaliphatic or heterocyclic amino or O-alkyl optionally substituted by a group selected from —OH, —COOH, —NH$_2$, —NHalkyl, —N(alkyl)$_2$, —SO$_3$H, —O-alkyl, Y and Y' independently from each other and from X and X' have the same meaning as X and X', m and n independently from each other have the value 1 or 2;

with the provisos that (i) if Y=Y' is a β-sulfoethylamino radical then X=X' is neither β-sulfoethylamino nor amino nor morpholino nor 3-(β-sulfatoethyl-sulfonyl)-phenylamino nor 3-sulfo-phenylamino (ii) if Y=Y' is morpholino then X=X' is neither morpholino nor 4-sulfo-phenylamino, and salts thereof as well as mixtures of such compounds are provided.

In preferred compounds, mixtures and salts thereof $R_1$ and $R_1'$ are halogen radicals, X, X', Y and Y' are optionally substituted aliphatic, aromatic, cycloaliphatic or heterocyclic amines and m and n have the value 1.

In most preferred compounds $R_1$ and $R_1'$ are chlorine and $R_2$ and $R_2'$ are hydrogen.

Examples for HX, HX', HY and HY' are monoethanolamine, diethanotamine, tetrahydro-1,4-oxazine, diethylaminopropylamine, 2-amino-propylamine, 1-amino-diethylaminoethane, 1-amino-dimethylaminopropane, N-(2-amino-ethyl)-tetrahydro-1,4-oxazine, N-(2-aminopropyl)-tetrahydro-1,4-oxazine, N,N-dibutylamino-propylamine, 3-methylamino-propylamine, 2-(3-aminopropyl)-aminoethanol, isopropylamino-ethylamine, N-(3-aminopropyl)-cyclohexyl-amine, N-(2-aminoethyl)-N-methylaniline, N,N-bis-(2-hydroxyethyl)-,2-diaminopropane, N-(2-aminoethyl)-pyrrolidine, N-(3-aminopropyl)-pyrrolidine, 2-piperidino-ethylamine, N-(2-aminoethyl)-piperazine, N-phenyl-piperazine, N-methyl-ethanolamine 3-methoxypropylamine, 1-methylamino-ethyl-2-sulphonic acid, 1-aminobenzene-2-sulfonic acid, 1-aminobenzene-3-sulfonic acid, 1-amino-benzene-4-sulfonic acid, 2-amino-benzoic acid, 3-amino-benzoic acid, 4-amino-benzoic acid, 3-amino-6-methoxy-benzoic acid, 5-amino-isophthalic acid, 2-amino-naphthaline-6-sulfonic acid and 2-aminonaphthaline-1-sulfonic acid.

According to another aspect of the invention a process for producing compounds of formula (I) is provided which is characterized in that a compound of formula (II)

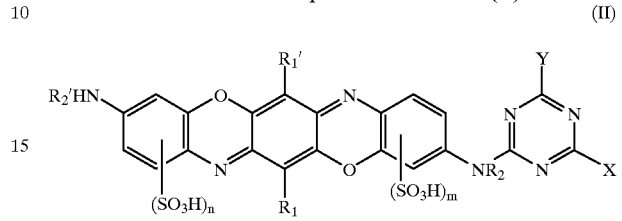

(II)

with the above-defined meanings of the symbols is reduced to the corresponding leuco form of formula (IIa)

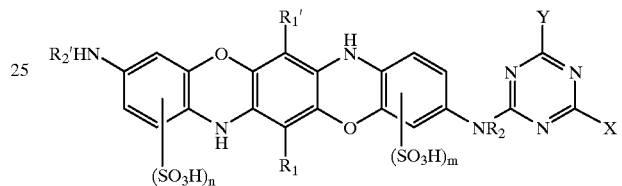

(IIa)

with the same meanings for the substituents as defined above, which is then reacted with one mole of the compound of formula (III)

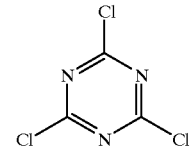

(III)

The remaining chlorine atoms of the triazine ring are replaced by X' and Y' by condensation and after oxidation a compound of formula (I) is obtained that can be isolated by known methods.

Depending on the meaning of X, X', Y and Y' the dioxazine compound can be symmetrically or asymmetrically substituted.

It is possible to prepare dioxazine compounds according to formula (I) with up to four different substituents attached to the triazine rings. In this way it is possible to design the compounds according to the desired needs. For example substituents with opposite ionogenicity may be introduced.

Alternatively, by replacement of all chlorine atoms with the same amino group, compounds with X=X'=Y=Y' may be obtained.

An alternative way to produce compounds according to formula (I) is to use triazine compounds according to formulae (IIIa) respectively (IIIb)

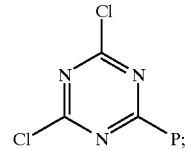

(IIIa)

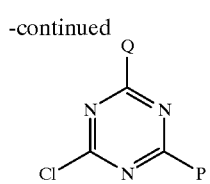

wherein P and Q signify X, X', Y or Y'as defined above.

Another procedure for producing the new dioxazine compounds is characterized in that first a compound of formula (IV)

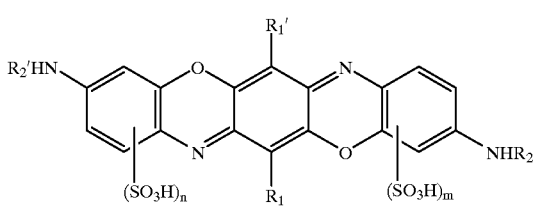

with the above defined meaning for $R_1$, $R_1'$, $R_2$, $R_2'$, m and n is reduced to the corresponding leuco form (V)

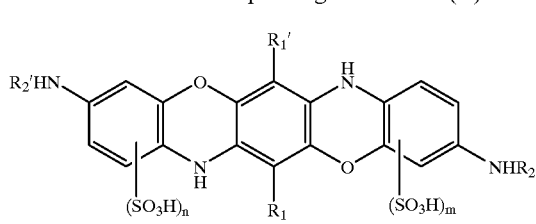

with the same definitions for substituents as defined above.

In the next step two moles of a compound of formula (III)

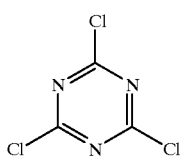

react with the compound of formula (V). The product of this reaction is a compound of formula (VI)

(IV)

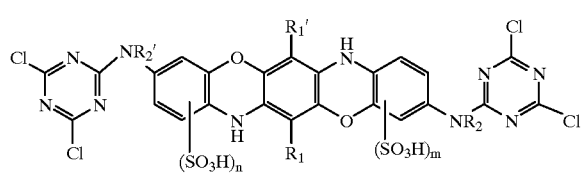

with the above-defined meanings of the symbols.

In the next steps first of all two moles of a compound HX or HX' and two moles of a compound HY or HY' are reacted with the compound of formula (VI). A compound according to formula (I) is then obtained after oxidation.

Depending upon the methods of synthesis and purification, the new dyestuff can be obtained in free- or salt form. When the new dyestuff is obtained in salt form, the cation associated therewith is not critical and may be any one of those non-chromophoric cations conventional in the field of dyes provided that the corresponding salts are water-soluble. Examples of such cations are alkali metal cations and unsubstituted and substituted ammonium cations, e.g. lithium, sodium, potassium, ammonium, mono-, di-, tri- and tetra-methylammonium, tri- ethylammonium and mono-, di- and tri- ethanolammonium. The preferred cations are the alkali metal cations and ammonium, with sodium or lithium being the most preferred.

In the procedure of producing the new triphendioxazine compounds the starting compound of formula (II) can be synthesized by known processes. Preferably in a first step the cyanuric chloride is condensed to triphendioxazine backbone at a temperature of 0–10° C. at a pH of 8–8.5. In a second step HX is condensed to the triazine ring at a temperature of 40–60° C. at a pH of 5.5–6.5 and in a third step HY is condensed to the triazine ring at a temperature between 90–95° C. at a pH of 8–8.5. As an alternative method mono- or bi-substituted cyanuric chlorides may be condensed to triphendioxazine backbone.

The reduction to the corresponding leuco form according to formula (IIa) respectively according to formula (V) can be done by known reducing agents under an inert gas atmosphere. Preferably powdery tin at room temperature is used at an acid pH value.

The condensation of the unsubstituted cyanuric chloride according to formula (III) with the corresponding leuco form according to formula (IIa) respectively according to formula (V) can be done under known conditions. Preferably at a pH between 5.5–6.5 and a temperature of 0–10° C. under an inert gas atmosphere.

The condensation of the mono-substituted cyanuric chloride according to formula (IIIa) with the corresponding leuco form according to formula (IIa) respectively according to formula (V) can be done under known conditions. Preferably at a pH between 5.5–6.5 and a temperature of 40–60° C. under an inert gas atmosphere.

The condensation of the bi-substituted cyanuric chloride according to formula (IIIb) with the corresponding leuco form according to formula (IIa) respectively according to formula (V) can be done under known conditions. Preferably at a pH between 5.5–8.5 and a temperature of 75–95° C. under an inert gas atmosphere.

The oxidation of the triphendioxazine compound is done by known oxidizing agent under known conditions. Preferred oxidizing agent is oxygen.

The isolation is done under known conditions. Preferably it is done by precipitation with NaCl or ethanol.

In a new dyestuff according to the invention, the cations can be the same or different, e.g., they can also be a mixture of the above mentioned cations meaning that the dyestuff can be in a mixed salt form.

The compounds according to the invention, mixtures thereof or their salts may be used for dyeing cationic dyeable materials such as: homo- or mixed-polymers of acrylonitrile, acid modified polyester or polyamide; wool; leather including low affinity vegetable-tanned leather; cotton; bast fibers such as hemp, flax, sisal, jute, coir and straw; regenerated cellulose fibers, glass or glass products comprising glass fibers; and substrates comprising cellulose for example paper and cotton. They may also be used for printing fibers, filaments and textiles comprising any of the above mentioned materials in accordance with known methods. Printing may be effected by impregnation of the material to be printed with a suitable printing paste comprising one or more compounds of the present invention. The type of printing paste employed may vary depending on the material to be printed. Choice of a suitable commercially available printing paste or production of a suitable paste is routine for one skilled in the art. Alternatively the compounds of the present invention may be used in the preparation of inks suitable for example for jet printing, in accordance with conventional methods.

Most preferably, the dyestuffs are used for dyeing or printing of paper e.g., sized or unsized, wood-free or wood-containing paper or paper-based products such as cardboard. They may be used in continuous dyeing in the stock, dyeing in the size press, in a conventional dipping or surface coloring process. The dyeing and printing of paper is effected by known methods.

The dyeings and prints and particularly those obtained on paper, show good fastness properties.

The compounds of formula (I) may be converted into dyeing preparations. Processing into stable liquid, preferably aqueous, or solid (granulated or powder form) dyeing preparations may take place in a generally known manner. Advantageously suitable liquid dyeing preparations may be made by dissolving the dyestuff or its salt in suitable solvents such as formamide, dimethylformamide, urea, glycols and ethers thereof, dextrin or addition products of boric acid with sorbitol which may be used together with water, optionally adding an assistant, e.g. a stabilizer. Such preparations may be obtained, for example, as described in French patent specification No. 1,572,030.

The compounds of formula (I) (in the corresponding salt form) have good solubility especially in cold water. Owing to their high substantivity the compounds of the present invention exhaust practically quantitatively and show a good build-up power. They can be added to the stock directly, i.e. without previously dissolving, as either a dry powder or granulate, without reducing the brilliance or the yield of color. They can also be used in soft water without loss of yield. They do not mottle when applied on paper, are not inclined to give two-sided dyeing on paper and are practically insensitive to filler or pH variations. They operate over a broad pH range, in the range of from pH 3 to 10. When producing sized or unsized paper, the waste water is essentially colorless. This feature, which is extremely important from an environmental viewpoint, when compared with similar known dyes, shows a marked improvement. A sized paper dyeing when compared with the corresponding unsized paper dyeing does not show any decrease in strength.

The paper dyeings or printings made with the compounds, in particular the metal-free forms, according to the invention are clear and brilliant and have very good light fastness: On exposure to light for a long time, the shade of the dyeing fades tone in tone. They show very good wet fastness properties; being fast to water, milk, fruit juice, sweetened mineral water, tonic water, soap and sodium chloride solution, urine etc. Furthermore, they have good alcohol fastness properties. The wet fastness properties are improved compared to known dyes showing otherwise similar properties. They do not exhibit a tendency towards two-sidedness.

Paper dyed or printed with the compounds of the present invention can be bleached oxidatively, a feature that is important for the recycling of waste and old paper/paper products. This property, together with the improved backwater results and wet-fastness, shows a marked improvement over known dyes having otherwise similar properties.

The compounds of the present invention may also be used to dye paper containing wood-pulp where even dyeings, having good fastness properties are obtained. Furthermore, they may be used for the production of coated paper in accordance with known methods. Preferably when coating, a suitable filler, for example kaolin, is employed in order to give a one-side coated paper.

The compounds of the present invention are also suitable for the use as ink-jet inks.

The compounds of the present invention are also suitable for dyeing in combination with other dyes for example other cationic or anionic dyes. The compatibility of the compounds of the present invention when used as a dye in mixtures with other commercially available dyes, may be determined according to conventional methods. The thus obtained dyeings have good fastness properties.

The invention further provides a substrate that has been dyed or printed with a compound of the present invention. The substrate may be selected from any of the above mentioned substrates. A preferred substrate is a substrate comprising cellulose such as cotton or paper or paper based product.

The following Examples further serve to illustrate the invention. In the Examples all parts and all percentages are by weight or volume, and the temperatures given are in degrees Celsius, unless indicated to the contrary.

EXAMPLE 1

136.3 parts of compound A

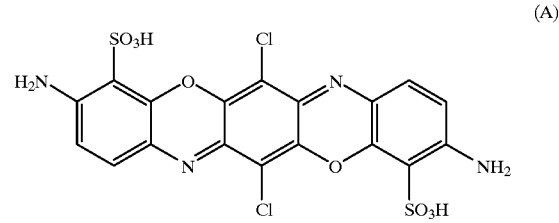

(A)

are reacted with 55 parts of cyanuric chloride (compound III) at pH 8–8.5 and at a temperature of 0–10° C. Afterwards 50 parts of 4-aminobenzene sulfonic acid are added at a pH of 5.5–6.5 and a temperature of 50° C. 27 parts of tetrahydro-1,4-oxazine are added at a pH of 8–8.5 and a temperature of 90–95° C. The nascent hydrochloride acid is neutralized by a 4 N LiOH solution. Compound B

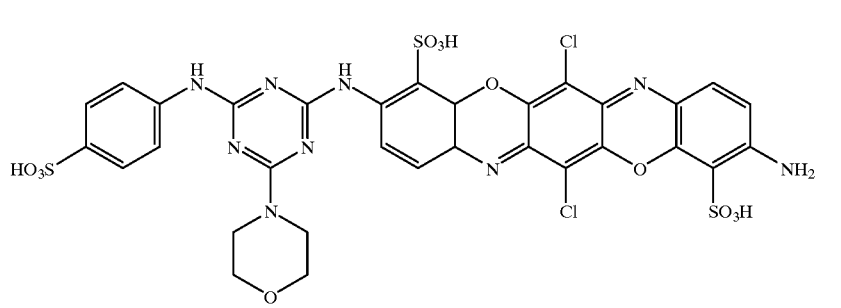

(B)

is obtained.

2500 parts of the compound B are suspended in 5 liter 5 M hydrochloride acid at room temperature under a nitrogen atmosphere. 50 parts of powdery tin are added to the suspension within 2 hours and the suspension is stirred until the color turns from blue-green to brown. Then the suspension is filtered and the filtrate is washed with 1 M hydrochloride acid. The moist presscake is kept under nitrogen. A compound of formula C

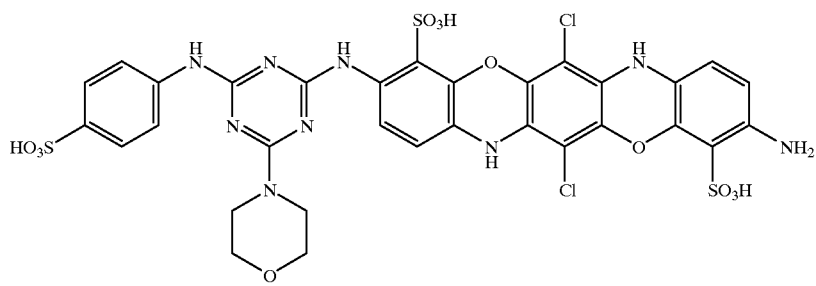
(C)

is obtained.

90 parts of compound D

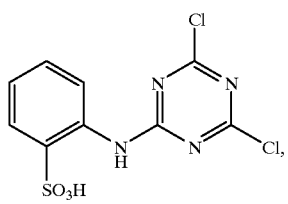
(D)

which is obtained by a condensation of compound (III) with 2-sulfophenylamino at a temperature of 0–10° C. and at a pH of 6.5–7.5, are added at a pH of 5.5–6 and at a temperature of 45–50° C. under a nitrogen atmosphere. The pH is adjusted by 4 N LiOH-solution.

3500 parts of a solution containing the compound E

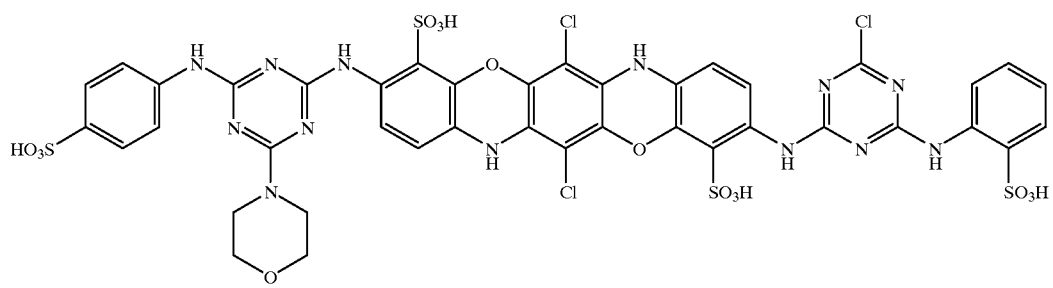
(E)

are obtained.

Afterwards the nitrogen atmosphere is removed and 50 parts of 1-methylamino-ethyl-2-sulfonic acid are added at a pH of 8–8.5 and a temperature of 90–95° C.; the reoxidation occurs simultaneously. The pH value is adjusted by a 4 N LiOH solution. The compound is precipitated by NaCl or ethanol and filtered and dried. 310 parts of a compound F

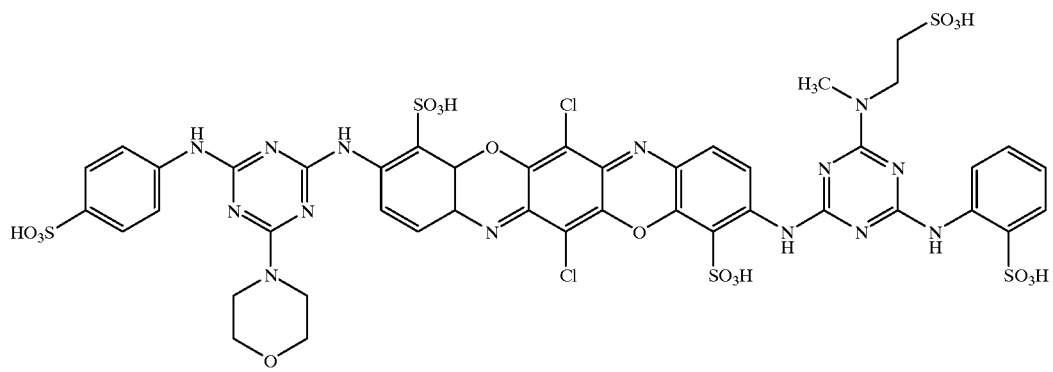
(F)

are obtained. The $\lambda_{max}$ is 555.9 nm (in water and 1% sodium acetate).

TABLE 1

Examples 2–67
Analogously to Example 1 the following examples are obtained.

[Structure: bis-triazinyl-aminosubstituted dioxazine dye with core bearing SO₃H, Cl, O, N substituents; X-triazine-Y group on left NH, X'-triazine-Y' group on right NH]

| Ex. | X—H | Y—H | X'—H | Y'—H | $\lambda_{max}$[1] |
|---|---|---|---|---|---|
| 2 | 4-aminobenzenesulfonic acid (H₂N–C₆H₄–SO₃H) | morpholine | 2-aminobenzenesulfonic acid (o-H₂N–C₆H₄–SO₃H) | H₃C–NH–CH₂CH₂–OH | 550.2 nm |
| 3 | " | " | " | HO–CH₂CH₂–NH–CH₂CH₂–OH | 550.4 nm |
| 4 | " | " | " | H₂N–CH₂CH₂CH₂–O–CH₃ | 549.9 nm |
| 5 | " | " | " | H₂N–CH₂CH₂–SO₃H | 551.8 nm |
| 6 | " | " | " | H₂N–CH₂CH₂CH₂–N(CH₂CH₃)₂ | 552.1 nm |
| 7 | " | " | 3-aminobenzenesulfonic acid (m-H₂N–C₆H₄–SO₃H) | H₂N–CH₂CH₂–OH | 550.3 nm |
| 8 | " | " | " | HO–CH₂CH₂–NH–CH₂CH₂–OH | 550.0 nm |
| 9 | " | " | " | H₂N–CH₂CH₂–SO₃H | 552.1 nm |
| 10 | " | " | " | H₃C–NH–CH₂CH₂–SO₃H | 552.4 nm |
| 11 | " | " | " | H₂N–CH₂CH₂CH₂–N(CH₂CH₃)₂ | 553.6 nm |
| 12 | " | " | 2-aminobenzoic acid (o-H₂N–C₆H₄–COOH) | H₂N–CH₂CH₂–OH | 551.7 nm |
| 13 | " | " | " | HO–CH₂CH₂–NH–CH₂CH₂–OH | 550.3 nm |

TABLE 1-continued

Examples 2–67
Analogously to Example 1 the following examples are obtained.

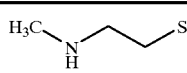

| Ex. | X—H | Y—H | X'—H | Y'—H | $\lambda_{max}$[1] |
|---|---|---|---|---|---|
| 14 | " | " | " | H₃C–NH–CH₂CH₂–SO₃H | 554.2 nm |
| 15 | " | " | " | H₂N–(CH₂)₃–N(C₂H₅)₂ | 556.3 nm |
| 16 | " | " | 3-H₂N–C₆H₄–COOH | H₂N–CH₂CH₂–OH | 550.1 nm |
| 17 | " | " | " | H₃C–NH–CH₂CH₂–SO₃H | 553.6 nm |
| 18 | " | " | " | H₂N–(CH₂)₃–N(C₂H₅)₂ | 554.3 nm |
| 19 | " | " | 4-H₂N–C₆H₄–COOH | H₂N–CH₂CH₂–OH | 550.0 nm |
| 20 | " | " | " | H₃C–NH–CH₂CH₂–SO₃H | 552.3 nm |
| 21 | " | " | " | H₂N–(CH₂)₃–N(C₂H₅)₂ | 553.1 nm |
| 22 | " | " | 5-H₂N-benzene-1,3-(COOH)₂ | HO–CH₂CH₂–NH–CH₂CH₂–OH | 549.8 nm |
| 23 | " | " | " | H₃C–NH–CH₂CH₂–SO₃H | 552.4 nm |
| 24 | " | " | " | H₂N–(CH₂)₃–N(C₂H₅)₂ | 553.7 nm |

TABLE 1-continued

Examples 2–67
Analogously to Example 1 the following examples are obtained.

[Structure: bis-triazinyl-aminosubstituted dioxazine chromophore with SO₃H, Cl, O, N substituents; X, Y on left triazine; X', Y' on right triazine]

| Ex. | X—H | Y—H | X'—H | Y'—H | $\lambda_{max}$[1] |
|-----|-----|-----|------|------|--------------------|
| 25 | " | " | 5-amino-2-methoxybenzoic acid (H₂N–C₆H₃(OCH₃)–COOH) | H₃C–NH–CH₂CH₂–OH | 552.3 nm |
| 26 | " | " | " | H₃C–NH–CH₂CH₂–SO₃H | 554.6 nm |
| 27 | " | " | " | H₂N–CH₂CH₂CH₂–N(CH₂CH₃)₂ | 556.3 nm |
| 28 | " | " | 2-amino-1-naphthalenesulfonic acid | H₂N–CH₂CH₂–OH | 560.1 nm |
| 29 | " | " | " | H₃C–NH–CH₂CH₂–OH | 561.2 nm |
| 30 | " | " | " | HO–CH₂CH₂–NH–CH₂CH₂–OH | 560.4 nm |
| 31 | " | " | " | H₂N–CH₂CH₂–SO₃H | 562.1 nm |
| 32 | " | " | " | H₃C–NH–CH₂CH₂–SO₃H | 562.7 nm |
| 33 | " | " | " | H₂N–CH₂CH₂CH₂–N(CH₂CH₃)₂ | 565.4 nm |
| 34 | " | " | 6-amino-2-naphthalenesulfonic acid | H₂N–CH₂CH₂–OH | 549.7 nm |
| 35 | " | " | " | HO–CH₂CH₂–NH–CH₂CH₂–OH | 550.1 nm |
| 36 | " | " | " | H₃C–NH–CH₂CH₂–SO₃H | 552.1 nm |

TABLE 1-continued

Examples 2–67
Analogously to Example 1 the following examples are obtained.

| Ex. | X—H | Y—H | X'—H | Y'—H | $\lambda_{max}$[1] |
|---|---|---|---|---|---|
| 37 | " | " | " | H₂N–CH₂CH₂CH₂–N(CH₂CH₃)(CH₂CH₃) (3-diethylaminopropylamine) | 553.8 nm |
| 38 | 3-aminobenzenesulfonic acid (H₂N–C₆H₄–SO₃H) | H₃C–NH–CH₂CH₂–OH | 2-aminobenzenesulfonic acid (H₂N–C₆H₄–SO₃H) | HO–CH₂CH₂–NH–CH₂CH₂–OH (diethanolamine) | 551.0 nm |
| 39 | " | " | " | morpholine | 551.1 nm |
| 40 | " | " | " | H₃C–NH–CH₂CH₂–SO₃H | 554.3 nm |
| 41 | " | " | 2-aminobenzoic acid (H₂N–C₆H₄–COOH) | H₂N–CH₂CH₂–OH | 553.1 nm |
| 42 | " | " | " | HO–CH₂CH₂–NH–CH₂CH₂–OH | 552.5 nm |
| 43 | " | " | " | H₃C–NH–CH₂CH₂–SO₃H | 554.1 nm |
| 44 | " | " | " | H₂N–CH₂CH₂CH₂–N(CH₂CH₃)(CH₂CH₃) | 557.0 nm |
| 45 | " | " | 4-aminobenzoic acid (H₂N–C₆H₄–COOH) | H₂N–CH₂CH₂–OH | 551.2 nm |
| 46 | " | " | " | morpholine | 550.1 nm |

TABLE 1-continued

Examples 2–67
Analogously to Example 1 the following examples are obtained.

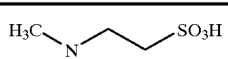

| Ex. | X—H | Y—H | X'—H | Y'—H | $\lambda_{max}{}^{1)}$ |
|---|---|---|---|---|---|
| 47 | " | " | " | H₃C–NH–CH₂CH₂–SO₃H | 554.8 nm |
| 48 | H₂N–C₆H₄–SO₃H (2-) | HO–CH₂CH₂–NH–CH₂CH₂–OH | H₂N–C₆H₄–COOH (2-) | H₂N–CH₂CH₂–OH | 553.0 nm |
| 49 | " | " | " | H₃C–NH–CH₂CH₂–SO₃H | 555.6 nm |
| 50 | " | " | " | H₂N–(CH₂)₃–N(C₂H₅)₂ | 557.3 nm |
| 51 | " | " | H₂N–C₆H₄–COOH (3-) | morpholine | 551.6 nm |
| 52 | " | " | " | H₂N–CH₂CH₂–SO₃H | 554.3 nm |
| 53 | " | " | " | H₃C–NH–CH₂CH₂–SO₃H | 554.7 nm |
| 54 | " | " | " | H₂N–(CH₂)₃–N(C₂H₅)₂ | 555.1 nm |
| 55 | " | " | H₂N–C₆H₄–COOH (4-) | morpholine | 550.2 nm |
| 56 | " | " | " | H₃C–NH–CH₂CH₂–SO₃H | 553.4 nm |
| 57 | " | " | " | H₂N–(CH₂)₃–N(C₂H₅)₂ | 554.9 nm |

TABLE 1-continued

Examples 2–67
Analogously to Example 1 the following examples are obtained.

| Ex. | X—H | Y—H | X'—H | Y'—H | $\lambda_{max}$[1] |
|---|---|---|---|---|---|
| 58 | " | " | 2-amino-naphthalene-1-sulfonic acid | H₂N-CH₂-CH₂-OH | 561.3 nm |
| 59 | " | " | " | morpholine (NH) | 560.7 nm |
| 60 | " | " | " | H₃C-NH-CH₂-CH₂-SO₃H | 563.2 nm |
| 61 | 2-amino-naphthalene-1-sulfonic acid | H₂N-CH₂-CH₂-OH | 2-aminobenzoic acid | HO-CH₂-CH₂-NH-CH₂-CH₂-OH | 560.7 nm |
| 62 | " | " | 5-aminoisophthalic acid | " | 558.3 nm |
| 63 | " | " | 4-aminobenzoic acid | " | 559.2 nm |
| 64 | " | " | H₃C-NH-CH₂-CH₂-SO₃H | " | 561.1 nm |
| 65 | " | " | " | morpholine (NH) | 561.8 nm |
| 66 | " | HO-CH₂-CH₂-NH-CH₂-CH₂-OH | " | H₃C-NH-CH₂-CH₂-SO₃H | 563.2 n |

TABLE 1-continued

Examples 2–67
Analogously to Example 1 the following examples are obtained.

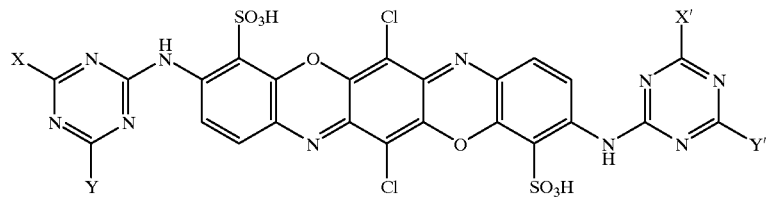

| Ex. | X—H | Y—H | X'—H | Y'—H | $\lambda_{max}$[1] |
|---|---|---|---|---|---|
| 67 | " | " | " | (morpholine) | 561.7 nm |

[1] all samples measured in water = 1% acetate

TABLE 2

Examples 68–112
Analogously to Example 1 the Examples according to the following formula

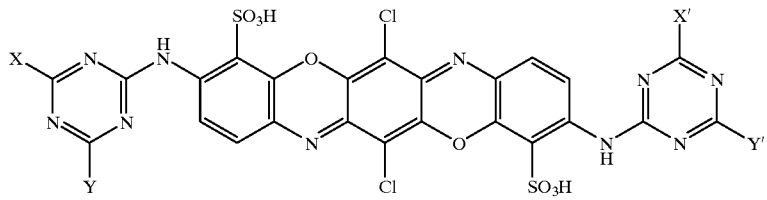

are obtainable.

| Ex. | X—H | Y—H | Y'—H | $\lambda_{max}$[1] |
|---|---|---|---|---|
| 68 | H$_2$N—C$_6$H$_4$—SO$_3$H | morpholine | HO-CH$_2$CH$_2$-NH-CH$_2$CH$_2$-OH | 549.4 nm |
| 69 | " | " | H$_3$C-NH-CH$_2$CH$_2$-SO$_3$H | 555.9 nm |
| 70 | " | " | H$_2$N-CH$_2$CH$_2$CH$_2$-N(CH$_3$)(C$_2$H$_5$)... N(CH$_2$CH$_3$)$_2$ with propyl | 546.9 nm |
| 71 | " | HO-CH$_2$CH$_2$-NH-CH$_2$CH$_2$-OH | H$_2$N-CH$_2$CH$_2$-OH | 550.1 nm |
| 72 | " | " | H$_3$C-NH-CH$_2$CH$_2$-SO$_3$H | 552.7 nm |
| 73 | " | " | H$_2$N-CH$_2$CH$_2$CH$_2$-N(C$_2$H$_5$)$_2$ | 553.0 nm |

TABLE 2-continued

Examples 68–112
Analogously to Example 1 the Examples according to the following formula

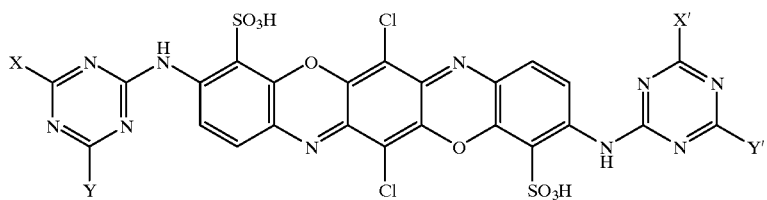

are obtainable.

| Ex. | X—H | Y—H | Y'—H | $\lambda_{max}$[1] |
|---|---|---|---|---|
| 74 | " | H₂N-CH₂CH₂-SO₃H | H₂N-CH₂CH₂-OH | 552.3 nm |
| 75 | " | " | H₂N-CH₂CH₂CH₂-O-CH₃ | 552.8 nm |
| 76 | " | H₃C-NH-CH₂CH₂-SO₃H | " | 552.5 nm |
| 77 | H₂N-C₆H₄-SO₃H (3-) | HO-CH₂CH₂-NH-CH₂CH₂-OH | H₃C-NH-CH₂CH₂-SO₃H | 552.7 nm |
| 78 | " | " | H₂N-CH₂CH₂CH₂-N(CH₂CH₃)₂ | 554.3 nm |
| 79 | " | morpholine | HO-CH₂CH₂-NH-CH₂CH₂-OH | 550.1 nm |
| 80 | " | " | H₂N-CH₂CH₂CH₂-N(CH₂CH₃)₂ | 554.2 nm |
| 81 | H₂N-C₆H₄-SO₃H (2-) | HO-CH₂CH₂-NH-CH₂CH₂-OH | H₂N-CH₂CH₂-OH | 549.8 nm |
| 82 | " | " | H₂N-CH₂CH₂CH₂-O-CH₃ | 550.2 nm |
| 83 | " | " | H₃C-NH-CH₂CH₂-SO₃H | 552.1 nm |
| 84 | " | morpholine | H₂N-CH₂CH₂-OH | 550.1 nm |

TABLE 2-continued

Examples 68–112
Analogously to Example 1 the Examples according to the following formula

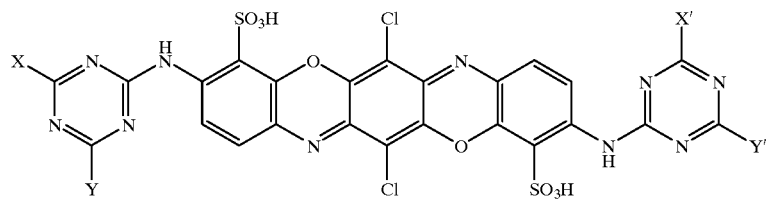

are obtainable.

| Ex. | X—H | Y—H | Y'—H | $\lambda_{max}$[1] |
|---|---|---|---|---|
| 85 | " | " | H₂N–CH₂CH₂CH₂–O–CH₃ | 550.3 nm |
| 86 | " | " | H₃C–NH–CH₂CH₂–SO₃H | 552.3 nm |
| 87 | 2-H₂N–C₆H₄–COOH | HO–CH₂CH₂–NH–CH₂CH₂–OH | morpholine | 550.4 nm |
| 88 | " | " | H₃C–NH–CH₂CH₂–SO₃H | 555.0 nm |
| 89 | " | " | H₂N–CH₂CH₂CH₂–O–CH₃ | 551.0 nm |
| 90 | " | " | H₃C–NH–CH₂CH₂–SO₃H | 554.3 nm |
| 91 | 3-H₂N–C₆H₄–COOH | HO–CH₂CH₂–NH–CH₂CH₂–OH | morpholine | 554.2 nm |
| 92 | " | " | H₃C–NH–CH₂CH₂–SO₃H | 557.0 nm |
| 93 | " | morpholine | H₂N–CH₂CH₂CH₂–O–CH₃ | 551.2 nm |
| 94 | " | " | H₃C–NH–CH₂CH₂–SO₃H | 556.9 nm |

TABLE 2-continued

Examples 68–112
Analogously to Example 1 the Examples according to the following formula

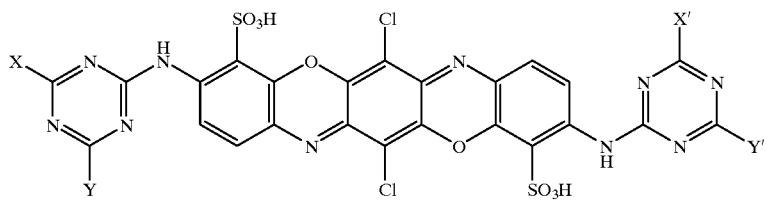

are obtainable.

| Ex. | X—H | Y—H | Y'—H | λ_max^{1)} |
|---|---|---|---|---|
| 95 | 5-amino-isophthalic acid (H₂N-C₆H₃(COOH)₂) | HO-CH₂CH₂-NH-CH₂CH₂-OH | morpholine | 551.4 nm |
| 96 | " | " | H₃C-NH-CH₂CH₂-SO₃H | 554.6 nm |
| 97 | " | morpholine | H₂N-CH₂CH₂CH₂-O-CH₃ | 550.3 nm |
| 98 | " | " | H₃C-NH-CH₂CH₂-SO₃H | 553.9 nm |
| 99 | 5-amino-2-methoxybenzoic acid | HO-CH₂CH₂-NH-CH₂CH₂-OH | morpholine | 552.7 nm |
| 100 | " | " | H₃C-NH-CH₂CH₂-SO₃H | 555.7 nm |
| 101 | " | morpholine | H₂N-CH₂CH₂CH₂-O-CH₃ | 551.4 nm |
| 102 | " | " | H₂N-CH₂CH₂-SO₃H | 556.1 nm |
| 103 | " | " | H₃C-NH-CH₂CH₂-SO₃H | 556.4 nm |
| 104 | 2-amino-naphthalene-1-sulfonic acid | H₂N-CH₂CH₂-OH | HO-CH₂CH₂-NH-CH₂CH₂-OH | 557.2 nm |

TABLE 2-continued

Examples 68–112
Analogously to Example 1 the Examples according to the following formula

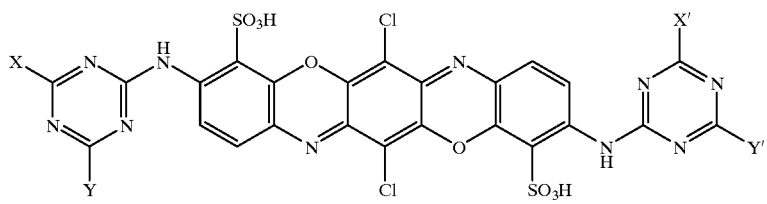

are obtainable.

| Ex. | X—H | Y—H | Y'—H | $\lambda_{max}$[1] |
|---|---|---|---|---|
| 105 | " | " | H₃C-NH-CH₂CH₂-SO₃H | 560.3 nm |
| 106 | " | HO-CH₂CH₂-NH-CH₂CH₂-OH | morpholine (NH) | 558.1 nm |
| 107 | " | " | H₃C-NH-CH₂CH₂-SO₃H | 561.2 nm |
| 108 | " | morpholine (NH) | " | 560.9 nm |
| 109 | 6-amino-2-naphthalenesulfonic acid | HO-CH₂CH₂-NH-CH₂CH₂-OH | H₂N-CH₂CH₂-OH | 550.7 nm |
| 110 | " | " | H₃C-NH-CH₂CH₂-SO₃H | 552.3 nm |
| 111 | " | morpholine (NH) | H₂N-CH₂CH₂CH₂-O-CH₃ | 550.0 nm |

TABLE 2-continued

Examples 68–112
Analogously to Example 1 the Examples according to the following formula

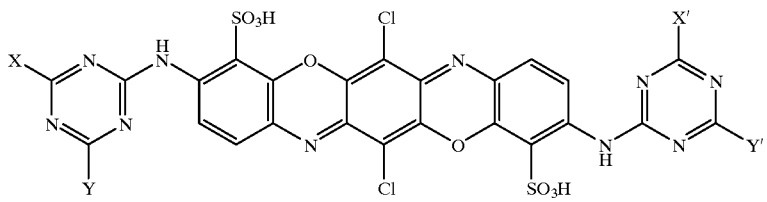

are obtainable.

| Ex. | X—H | Y—H | Y'—H | $\lambda_{max}$ [1] |
|---|---|---|---|---|
| 112 | " | " |  | 553.1 nm |

[1] all samples measured in water = 1% acetate

EXAMPLE 113

1. Preparation of Intermediate G 136.3 parts of compound A

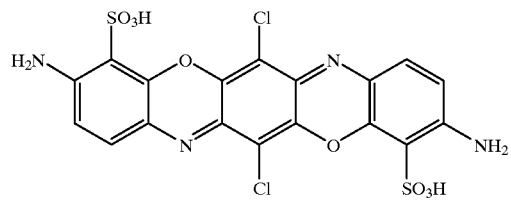
(A)

are suspended in 5 liter 5 M hydrochloride acid at room temperature under a nitrogen atmosphere. 50 parts of powdery tin are added to the suspension within 2 hours and the suspension is stirred until the color turns from blue-green to brown. Then the suspension is filtered and the filtrate is washed with I M hydrochloride acid. The moist filtrate is kept under nitrogen. 440 parts of this moist filtrate of formula G are obtained.

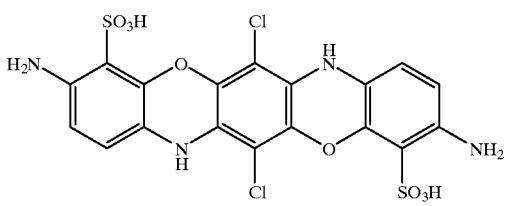
(G)

2. Preparation of Intermediate J 440 parts of the moist filtrate of the compound of formula G are suspended in 2500 parts of water under a nitrogen atmosphere at room temperature. The pH-value is adjusted at 6 with a 4 N LiOH-solution. 200 parts of compound H

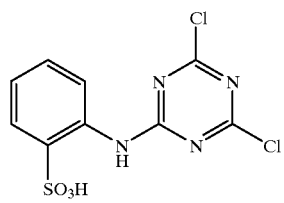
(H)

are added to suspension and the suspension is stirred at a temperature of 45–50° C. and a pH of 5.5–6 until all educts have reacted. A compound of fonnula J is obtained.

(J)

3. Preparation of Example 113

65 parts of a compound with the formula E

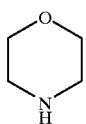

(K)

are added to 5300 parts of a solution with 0.25 mol of the compound J at 50° C. and the solution is heated up to 90–95° C. The pH is kept at 8–8.5 with a 4 N LiOH-solution. A dyestuff of formnula L is obtained after an oxidation and a precipitation with NaCl or ethanol. Its $\lambda_{max}$ is 550.2 nm (in water and 1% sodium acetate).

5300 parts of an aqueous solution containing 0.25 mol of the compound M are mixed with 100 parts of 1-methylamino-ethyl-2-sulfonic acid at 50° C. The solution is heated up to 90–95° C. and the pH is kept at 8–8.5 by a 4 N LiOH-solution. After the oxidation and filtration 6000 parts of the solution are ultrafiltered by a suitable membrane such as e.g. G10, G20 or G50. The solution is now concentrated to 4000 parts. This obtained liquid dyestuff formulation of the compound of formula 0 contains only traces of inorganic salts and shows an excellent storing property.

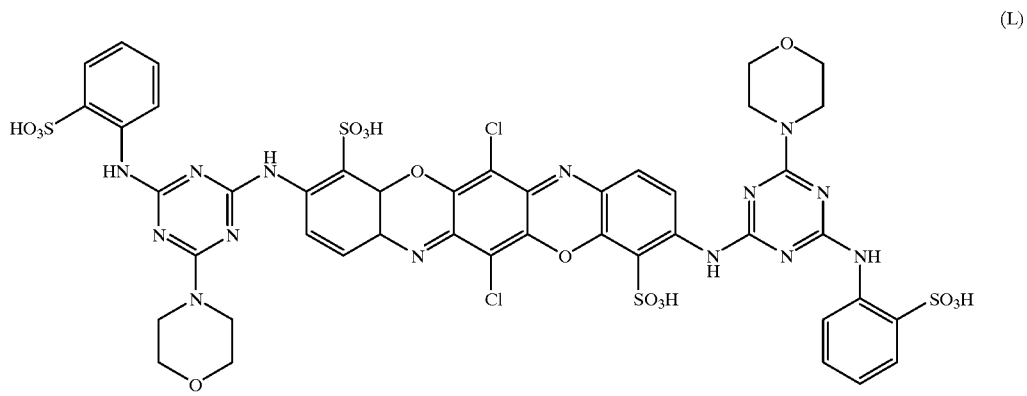

(L)

EXAMPLE 114

Analogously to Example 113 440 parts of the moist filtrate of formula M are added to 230 parts of compound G

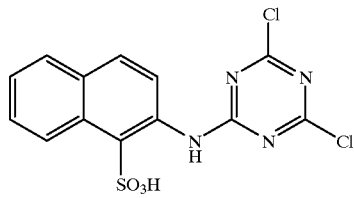

(M)

and the solution is stirred under a nitrogen atmosphere at pH 5.5–6 and a temperature of 45–50° C. A compound of formula N is obtained.

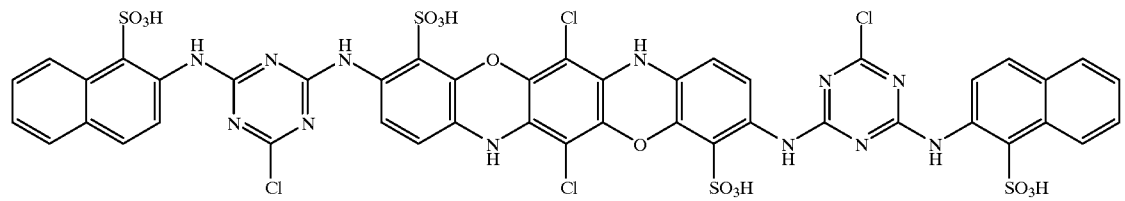

(N)

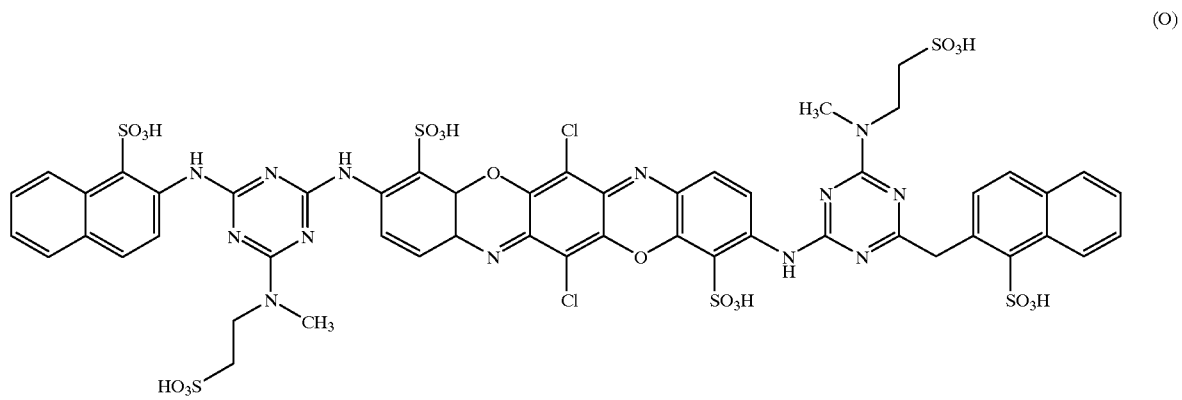

(O)

The λ$_{max}$ of this formulation is 556.7 nm (in water and 1% sodium acetate).

EXAMPLE 115

Analogously to Example 113 440 parts of the moist filtrate of formula G are mixed to 233 parts of the compound P

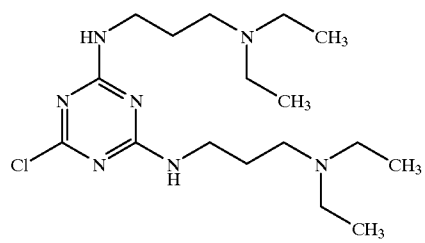

(P)

The solution is heated up to 95° C. and stirred at a pH of 5.5–6 under a nitrogen atmosphere. Afterwards the leuco form is oxidized by oxygen. The dyestuff of formula R is filtered and washed by water. 300 parts of the dyestuff are obtained. This dyestuff is soluble in common organic acids such as e.g. lactic acid, formic acid or acetic acid and stable liquid dyestuff formulations are obtained. The λ$_{max}$ value of this formulation is 656.6 nm (in DIF and 1% glacial acetic acid).

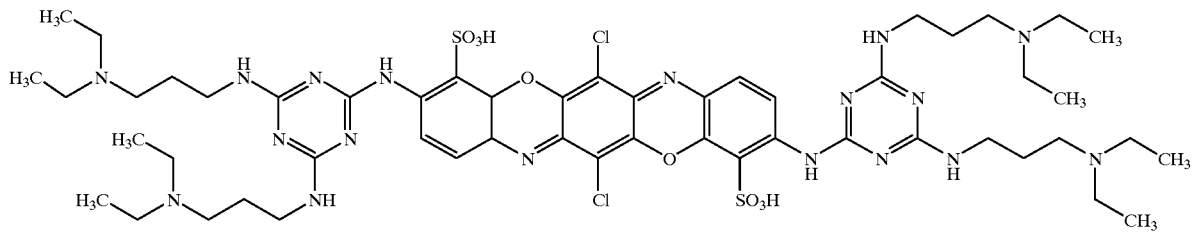

(R)

TABLE 3

Example 116–194
Analogously to the examples 113–115 the following compounds are obtainable.

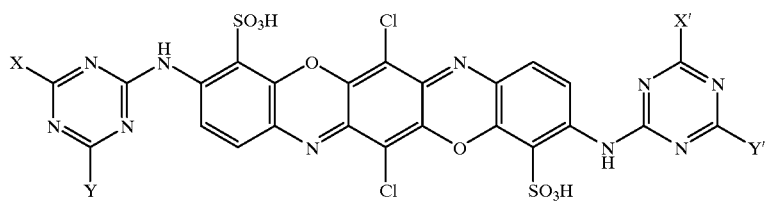

| Ex. | X—H | Y—H | λ_max^1) |
|---|---|---|---|
| 116 | H₂N−CH₂CH₂−OH | H₃C−NH−CH₂CH₂−OH | 554.3 nm |
| 117 | " | H₂N−CH₂CH₂CH₂−O−CH₃ | 546.1 nm |
| 118 | " | HO−CH₂CH₂−NH−CH₂CH₂−OH | 544.2 nm |
| 119 | " | H₂N−CH₂CH₂−SO₃H | 547.0 nm |
| 120 | " | H₃C−NH−CH₂CH₂−SO₃H | 547.3 nm |
| 121 | " | 2-aminobenzenesulfonic acid | 549.6 nm |
| 122 | " | 3-aminobenzenesulfonic acid | 549.9 nm |
| 123 | " | 4-aminobenzenesulfonic acid | 549.1 nm |
| 124 | " | 2-aminobenzoic acid | 554.4 nm |
| 125 | " | 3-aminobenzoic acid | 557.2 nm |
| 126 | " | 4-aminobenzoic acid | 557.4 nm |

TABLE 3-continued
Example 116–194
Analogously to the examples 113–115 the following compounds are obtainable.
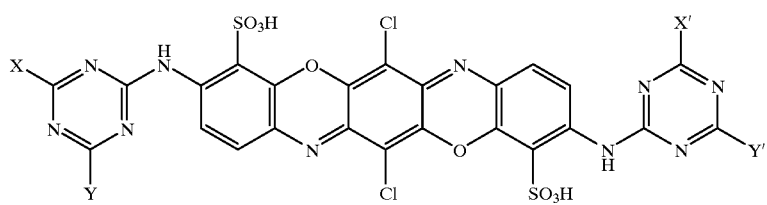
| Ex. | X—H | Y—H | $\lambda_{max}$[1] |
|---|---|---|---|
| 127 | " | 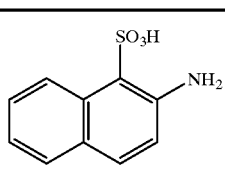 | 560.1 nm |
| 128 | " | 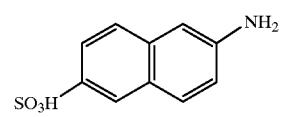 | 549.6 nm |
| 129 | HOCH₂CH₂NHCH₂CH₂OH | 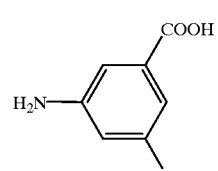 | 548.1 nm |
| 130 | " | H₃C—NH—CH₂CH₂—SO₃H | 549.6 nm |
| 131 | " | 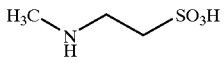 | 550.4 nm |
| 132 | " | 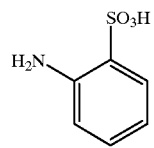 | 550.7 nm |
| 133 | " | 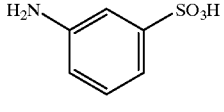 | 549.2 nm |
| 134 | " | 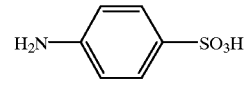 | 550.3 nm |
| 135 | " | 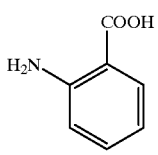 | 551.9 nm |

TABLE 3-continued

Example 116–194
Analogously to the examples 113–115 the following compounds are obtainable.

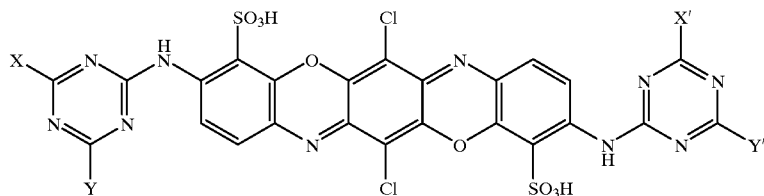

| Ex. | X—H | Y—H | $\lambda_{max}$[1] |
|---|---|---|---|
| 136 | " | H₂N—C₆H₄—COOH (para) | 553.5 nm |
| 137 | " | 5-amino-2-methoxybenzoic acid | 554.2 nm |
| 138 | " | 5-aminoisophthalic acid | 553.9 nm |
| 139 | " | 2-amino-1-naphthalenesulfonic acid | 557.3 nm |
| 140 | " | 6-amino-2-naphthalenesulfonic acid | 546.9 nm |
| 141 | morpholine | H₂N(CH₂)₃OCH₃ | 546.0 nm |
| 142 | " | H₂NCH₂CH₂SO₃H | 548.0 nm |
| 143 | " | 3-aminobenzenesulfonic acid | 550.1 nm |
| 144 | " | anthranilic acid | 551.0 nm |

TABLE 3-continued

Example 116–194
Analogously to the examples 113–115 the following compounds are obtainable.

| Ex. | X—H | Y—H | $\lambda_{max}$[1) |
|---|---|---|---|
| 145 | " | H₂N–C₆H₄–COOH (3-amino benzoic acid) | 552.9 nm |
| 146 | " | H₂N–C₆H₄–COOH (4-amino benzoic acid) | 559.7 nm |
| 147 | " | 5-amino isophthalic acid | 553.4 nm |
| 148 | " | 5-amino-2-methoxy benzoic acid | 569.9 nm |
| 149 | " | 2-amino naphthalene-1-sulfonic acid | 543.9 nm |
| 150 | " | 6-amino naphthalene-2-sulfonic acid | 548.2 nm |
| 151 | H₃C–NH–CH₂CH₂–SO₃H | H₂N–CH₂CH₂CH₂–O–CH₃ | 548.3 nm |
| 152 | " | 2-amino benzenesulfonic acid | 552.4 nm |
| 153 | " | 4-amino benzenesulfonic acid | 551.4 nm |

TABLE 3-continued
Example 116–194
Analogously to the examples 113–115 the following compounds are obtainable.
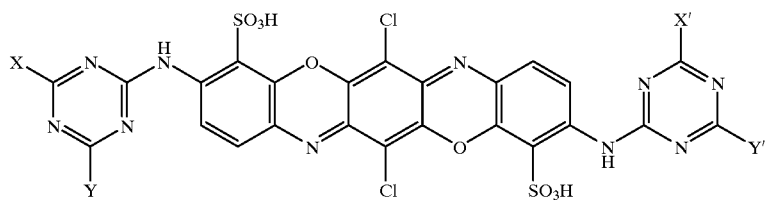
| Ex. | X—H | Y—H | $\lambda_{max}$[1) |
|---|---|---|---|
| 154 | " | 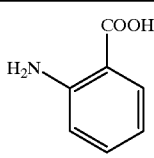 | 556.1 nm |
| 155 | " | 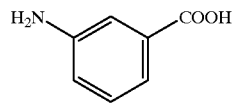 | 557.5 nm |
| 156 | " | 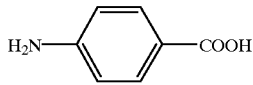 | 565.2 nm |
| 157 | " | 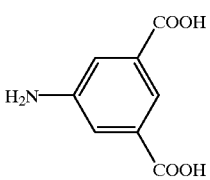 | 583.0 nm |
| 158 | " | 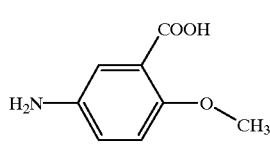 | 556.8 nm |
| 159 | " | 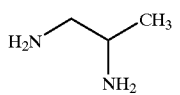 | 560.1 nm |
| 160 | 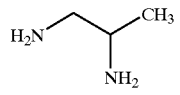 | " | 558.8 nm |
| 161 | 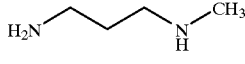 | 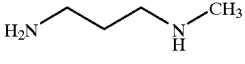 | 557.4 nm |
| 162 | 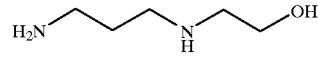 | 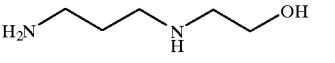 | 563.6 nm |
| 163 | 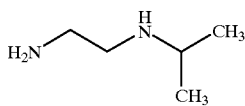 | 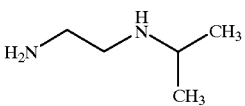 | 558.3 nm |

TABLE 3-continued

Example 116–194
Analogously to the examples 113–115 the following compounds are obtainable.

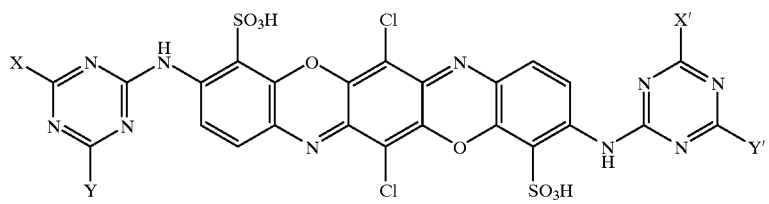

| Ex. | X—H | Y—H | λ_max^{1)} |
|---|---|---|---|
| 164 | H₂N−CH₂CH₂−N(C₂H₅)₂ | H₂N−CH₂CH₂−N(C₂H₅)₂ | 559.8 nm |
| 165 | H₂N−(CH₂)₃−N(CH₃)₂ | H₂N−(CH₂)₃−N(CH₃)₂ | 560.1 nm |
| 166 | H₂N−(CH₂)₃−N(n-Bu)₂ | H₂N−(CH₂)₃−N(n-Bu)₂ | 559.7 nm |
| 167 | H₂N−(CH₂)₃−N(CH₂CH₂OH)₂ | H₂N−(CH₂)₃−N(CH₂CH₂OH)₂ | 569.0 nm |
| 168 | H₂N−CH₂CH₂−pyrrolidinyl | H₂N−CH₂CH₂−pyrrolidinyl | 561.3 nm |
| 169 | H₂N−CH₂CH₂−piperidinyl | H₂N−CH₂CH₂−piperidinyl | 564.2 nm |
| 170 | H₂N−CH₂CH₂−piperidinyl | H₂N−CH₂CH₂−piperidinyl | 563.1 nm |
| 171 | H₂N−CH₂CH₂−piperazinyl-NH | H₂N−CH₂CH₂−piperazinyl-NH | 562.2 nm |
| 172 | H₂N−CH₂CH₂−morpholinyl | H₂N−CH₂CH₂−morpholinyl | 563.7 nm |
| 173 | H₂N−(CH₂)₃−morpholinyl | H₂N−(CH₂)₃−morpholinyl | 559.4 nm |

TABLE 3-continued

Example 116–194
Analogously to the examples 113–115 the following compounds are obtainable.

[Structure: triazine-substituted dioxazine core with SO₃H, Cl substituents, bearing X/Y and X'/Y' groups on triazines]

| Ex. | X—H | Y—H | $\lambda_{max}$[1)] |
|---|---|---|---|
| 174 | $H_2N$-propyl-NH-cyclohexyl | $H_2N$-propyl-NH-cyclohexyl | 558.7 nm |
| 175 | $H_2N$-ethyl-N(CH₃)-phenyl | $H_2N$-ethyl-N(CH₃)-phenyl | 568.2 nm |
| 176 | $H_2N$-propyl-N(CH₂CH₃)₂ | $H_2N$-CH(CH₃)-CH₂-NH₂ (or $H_2N$-CH₂-CH(CH₃)-NH₂) | 561.0 nm |
| 177 | " | $H_2N$-propyl-NH-CH₃ | 560.4 nm |
| 178 | " | $H_2N$-propyl-N(CH₂CH₂OH)₂ | 562.1 nm |
| 179 | " | $H_2N$-ethyl-N(CH₂CH₃)₂ | 559.7 nm |
| 180 | " | $H_2N$-propyl-N(CH₃)₂ | 562.4 nm |
| 181 | " | $H_2N$-ethyl-morpholine | 565.8 nm |
| 182 | " | $H_2N$-propyl-morpholine | 562.3 nm |

TABLE 3-continued

Example 116–194
Analogously to the examples 113–115 the following compounds are obtainable.

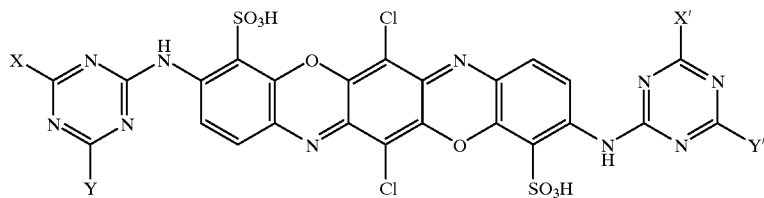

| Ex. | X—H | Y—H | $\lambda_{max}$[1] |
|---|---|---|---|
| 183 | " | H₂N–CH₂CH₂–N(CH₃)–C₆H₅ | 566.7 nm |
| 184 | H₂N–(CH₂)₃–N(CH₃)₂ | " | 565.9 nm |
| 185 | " | H₂N–CH₂CH₂–morpholine | 561.0 nm |
| 186 | " | H₂N–(CH₂)₃–morpholine | 560.0 nm |
| 187 | " | HO–CH₂CH₂–NH–CH₂CH₂–OH | 561.7 nm |
| 188 | " | H₂N–(CH₂)₃–N(CH₂CH₂OH)₂ | 562.1 nm |
| 189 | H₂N–CH₂CH₂–N(C₂H₅)₂ | H₂N–CH₂CH₂–NH–CH(CH₃)₂ | 558.7 nm |
| 190 | " | H₂N–(CH₂)₃–NH–CH₃ | 559.5 nm |
| 191 | HO–CH₂CH₂–NH–CH₂CH₂–OH | H₂N–(CH₂)₃–NH–CH₃ | 561.0 nm |
| 192 | H₂N–CH₂CH₂–pyrrolidine | H₂N–(CH₂)₃–N(CH₂CH₂OH)₂ | 563.1 nm |
| 193 | " | H₂N–CH₂CH₂–NH–CH(CH₃)₂ | 559.1 nm |

TABLE 3-continued

Example 116–194
Analogously to the examples 113–115 the following compounds are obtainable.

| Ex. | X—H | Y—H | $\lambda_{max}$[1) |
|---|---|---|---|
| 194 | HN(piperazine)N-phenyl | HN(piperazine)N-phenyl | 552.1 nm |

[1) all samples measured in water = 1% acetate

APPLICATION EXAMPLE A 70 parts of chemically bleached sulphite cellulose of pinewood and 30 parts of chemically bleached sulphite cellulose of birchwood are ground in a Hollander in 2000 parts of water. 0.2 parts of the dyestuff of Example 1 are sprinkled into this pulp. After mixing for 20 minutes, paper is produced therefrom. The absorbent paper obtained in this way is dyed (reddish) blue. The waste water is practically colorless.

APPLICATION EXAMPLE B 0.5 parts of the dyestuff powder of Example 1 are dissolved in 100 parts of hot water and cooled to room temperature. The solution is added to 100 parts of chemically bleached sulphite cellulose, which have been ground in a Hollander with 2000 parts of water. After thorough mixing for 15 minutes, sizing takes place in the usual way with rosin size and aluminum sulfate. Paper that is produced from this material has a (reddish) blue shade, and has good wastewater and wet fastness, as well as good light fastness.

APPLICATION EXAMPLE C

An absorbent length of unsized paper is drawn through a dyestuff solution of the following composition at 40–50° C.:

| | |
|---|---|
| 0.5 | parts of the dyestuff of Example 1 |
| 0.5 | parts of starch and |
| 99.0 | parts of water. |

The excess dyestuff solution is squeezed out through two rollers. The dried length of paper is dyed (reddish) blue.

Dyeing may also take place in a similar manner to that of examples A to C using the dyestuffs of Examples 2 to 194 or respectively a dye preparation thereof. The paper dyeings obtained are red and have a high level of fastness.

APPLICATION EXAMPLE D 50 parts of bleached pinewood sulphite cellulose and 50 parts of bleached beech cellulose (degree of beating 30 SR*) are mixed with 0.5 parts of the dyestuff of Example 1 in water (pH 4, water hardness 10 dH). After 16 minutes, sheet formation takes place. The paper is dyed in an intense reddish-yellow shade. In contrast, a dyeing made at pH 7 shows no variation in depth or shade. The rate of exhaustion reaches 100% and the waste water is colorless.

*) SR=Schopper Riegler degree

In a similar manner as described in Application Example D the dyestuffs according to Examples 2–194 may be used for dyeing bleached beech cellulose.

APPLICATION EXAMPLE E 100 parts of intermediate-dried chrome velours leather are drummed for one hour at 50 in a drum containing a bath of 400 parts of water, 2 parts of 25% ammonium hydroxide solution and 0.1 parts of a commercial wetting agent. The bath is subsequently drained. 400 parts of water of 60° C. and 1 part of 25% ammonium hydroxide solution are added to the drummed chrome velours leather that is still moist. After adding 5 parts of the dyestuff of Example 1, dissolved in 200 parts of water, dyeing is effected for 90 minutes at 60° C. Then 50 parts of 8 % formic acid are slowly added in order to acidify the pH. The treatment is then continued for a further 30 minutes. Finally, the leather is rinsed, dried and finished in the usual way. The red leather dyeing obtained is level.

In a similar manner as described in Application Example E the dyestuffs according to Examples 2–194 may be used for dyeing intermediate-dried chrome velours.

APPLICATION EXAMPLE F 1.1 parts of the dyestuff of Example 1 are dissolved at 60° C. in 100 parts of demineralized water and subsequently diluted with 900 parts of cold, demineralized water. Then, 100 parts of cotton tricot (bleached) are added to the dye bath. After 5 minutes, 10 parts of calcined sodium sulphate and 2 parts of ammonium sulphate are added. During 70 minutes, the temperature of the dye bath is continuously raised to 98° C. This temperature is maintained for 20 minutes and the dye bath is then cooled to 70° C. over the course of 30 minutes. The dyed material is rinsed for 2 minutes firstly with cold, demineralized water, and subsequently for 2 minutes with cold tap water, then centrifuged and dried. The cotton dyeing obtained is red. In a similar manner as described in Application Example F the dyestuffs according to Examples 2–194 may be used for dyeing cotton tricot.

APPLICATION EXAMPLE G 100 parts of cotton tricot, which have been dyed with the dyestuff of Example 1 analogously to the method of Application Example F in ca. 1/1standard depth, are mixed without intermediate drying in 1000 parts of tap water at 25° C. with 5 parts of sodium chloride and 4 parts of an after-treatment agent obtained from the reaction of diethylenetriamine with dicyandiamide. The pH value of the dye bath is set at 6.5–7. The bath is heated to 60° C. over the course of 20 minutes, and this temperature is maintained for a further 20 minutes. Afterwards, the material is rinsed with cold tap water. The red cotton dyeing which has been after-treated in this way has perfect washing fastness and very good light fastness.

In a similar manner as described in Application Example G the dyestuffs according to Examples 2–194 may be used for dyeing cotton tricot.

APPLICATION EXAMPLE H

A cotton dyeing produced with the dyestuff of Example 1 analogously to the method of Application Example F in 1/1 standard depth, is impregnated on a padder with a solution, which contains 100 g/l of an after-treatment agent obtained by reacting the after-treatment agent of Application Example G with dimethyloldihydroxyethyleneurea and a hardening catalyst, and it is squeezed out to a pick-up of ca. 80%. It is subsequently shock-dried for 45 seconds on a stenter at a temperature of 175–180° C. The yellow cotton dyeing thus obtained is notable for its perfect washing fastness. At the same time, there is a considerable improvement in the creasing fastness, and reduced swelling value of the cellulosic fibres. In a similar manner as described in Application Example H the dyestuffs according to Examples 2–194 may be used for dyeing cotton.

APPLICATION EXAMPLE I

A printing paste having the components

| 40 | parts of the dyestuff of Example 1 |
| 100 | parts of urea |
| 330 | parts of water |
| 500 | parts of a 4% sodium alginate thickener |
| 10 | parts of the sodium salt of 1-nitrobenzene-3-sulphonic acid |
| 20 | parts of soda |
| 1000 | parts in all | is applied to cotton material by conventional printing processes. The printed and dried material is steamed for 4–8 minutes at 102–105° C. and then given a cold and a hot rinse. The fixed cotton material is subsequently washed at the boil. In a similar manner as described in Application Example I the dyestuffs according to Examples 2–194 may be used for dyeing cotton.

APPLICATION EXAMPLE J 12.6 parts dyestuff solution of Example 114 are added dropwise at room temperature to a stirred mixture of 20.0 parts diethyleneglycole and 67.4 parts of demineralized water. The resulting ink exhibits good light- and waterfastness properties. In similar manner as described in Application Example J all the Examples of Table 1 and Table 2 and Table 3 may be used.

What is claimed is:

1. Compounds of formula (I)

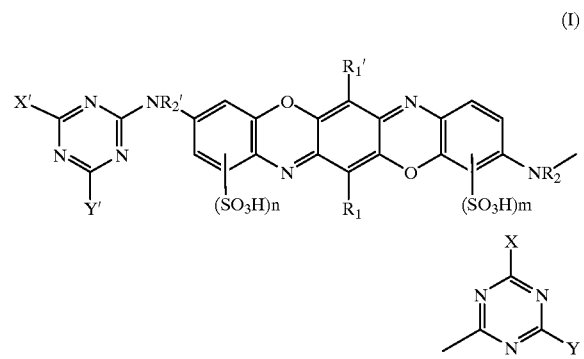

wherein $R_1$ and $R_1'$ independently from each other are hydrogen or halogen, $R_2$ and $R_2'$ independently from each other are hydrogen or $C_{1-4}$-alkyl, X and X' independently from each other are the rest of an amine of the group monoethanolamine, diethanolamine, tetrahydro-1,4-oxazine, diethylaminopropylamine, 2-amino-propylamine, 1-amino-diethylaminoethane, 1-amino-dimethylaminopropane, N-(2-amino-ethyl)-tetrahydro-1,4-oxazine, N-(2-aminopropyl)-tetrahydro-1,4-oxazine, N,N-dibutylamino-propylamine, 3-methylamino-propylamine, 2-(3-aminopropyl)-aminoethanol, isopropylamino-ethylamine, N-(3-aminopropyl)-cyclohexyl-amine, N-(2-aminoethyl)-N-methylaniline, N,N-bis-(2-hydroxyethyl)-1,3-diaminopropane, N-(2-aminoethyl)-pyrrolidine, N-(3-aminopropyl)-pyrrolidine, 2-piperidino-ethylamine, N-(2-arninoethyl)-piperazine, N-phenyl-piperazine, N-methyl-ethanolamine 3-methoxypropyl-amine, 1-methylamino-ethyl-2-sulphonic acid, 1-aminobenzene-2-sulfonic acid, 1-amino-benzene-3-sulfonic acid, 1-amino-benzene-4-sulfonic acid, 2-amino-benzoic acid, 3-amino-benzoic acid, 4-amino-benzoic acid, 3-amino-6-methoxy-benzoic acid, 5-amino-isophthalic acid, 2-amino-naphthaline-6-sulfonic acid and 2-aminonaphthaline-1-sulfonic acid, Y and Y' independently from each other and from X and X' have the same meaning as X and m and n independently from each other have the value 1 or 2;

with the provisos that (i) if Y=Y' is morpholino radical then X=X' is neither morpholino nor 4-sulfo-phenylamino, and salts thereof as well as mixtures of such compounds.

2. Compounds according to claim 1 wherein $R_1$ and $R_1'$ are chlorine radicals and $R_2$ and $R_2'$ are hydrogen and salts thereof as well as mixtures of such compounds.

3. Compounds according to the following formulae

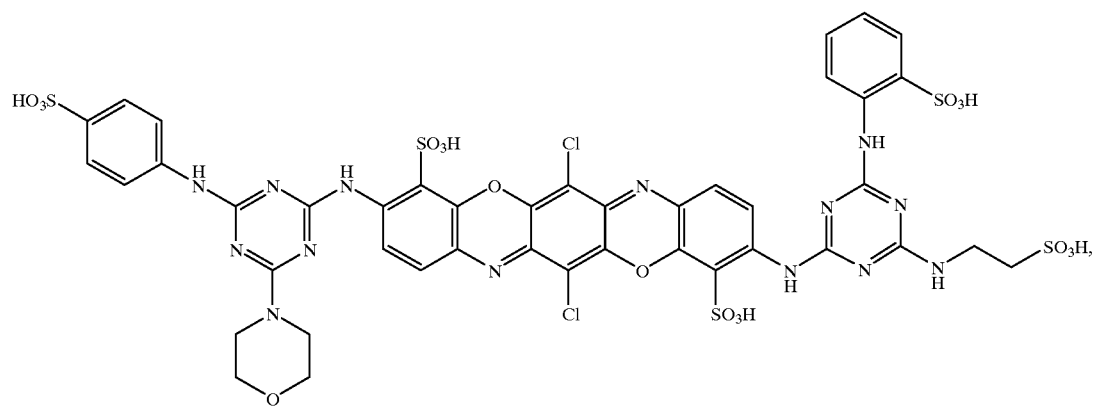
(a)
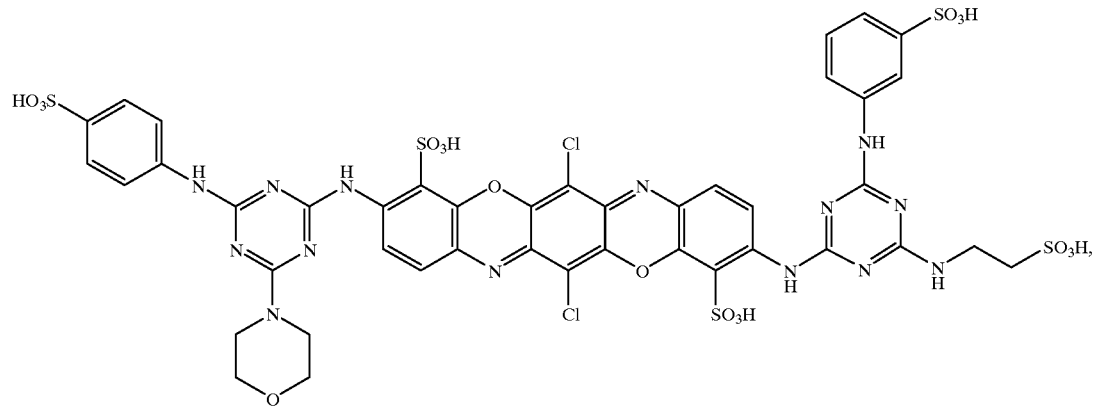
(b)
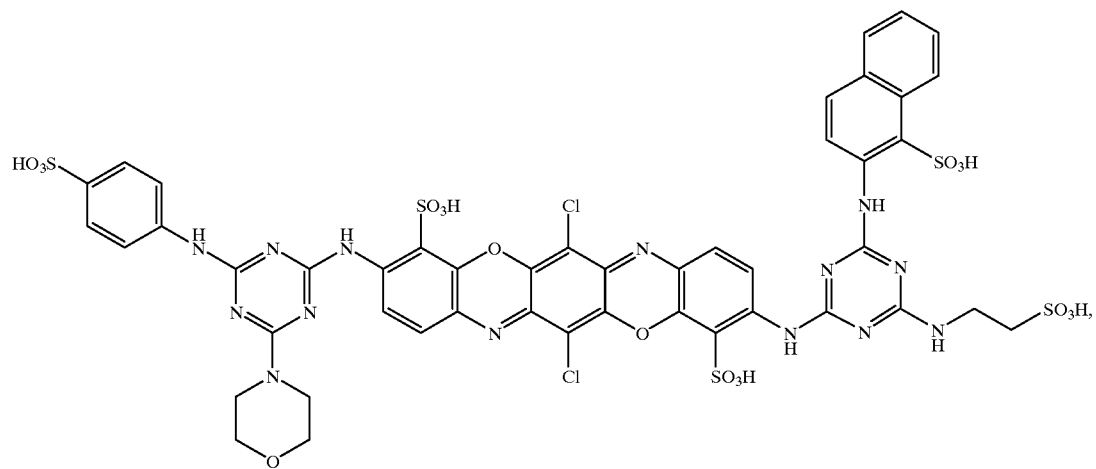
(c)
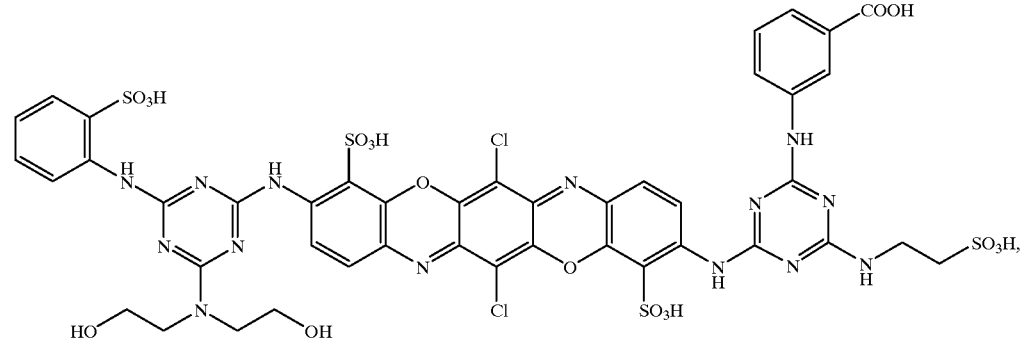
(d)

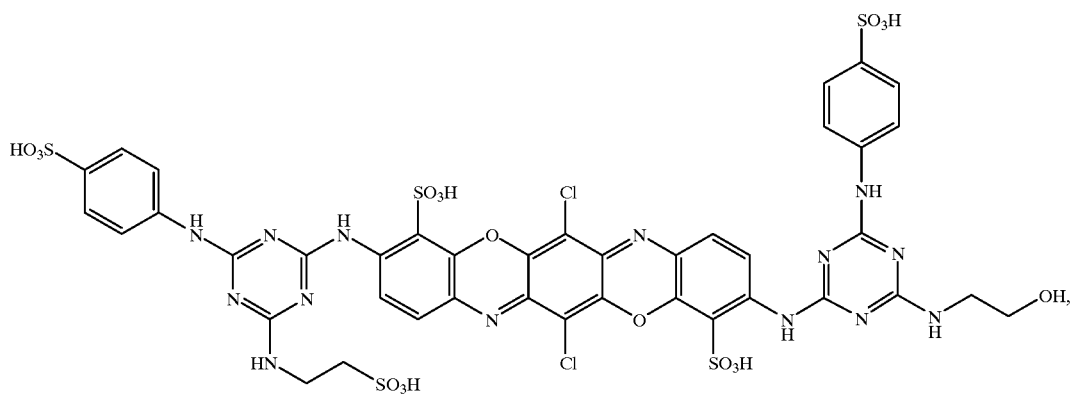
(e)
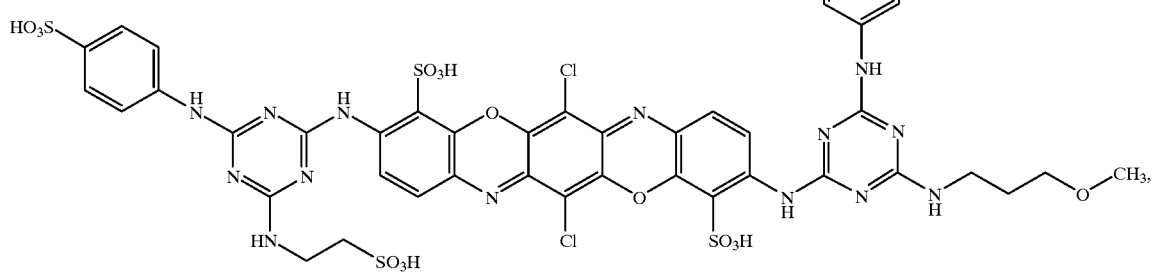
(f)
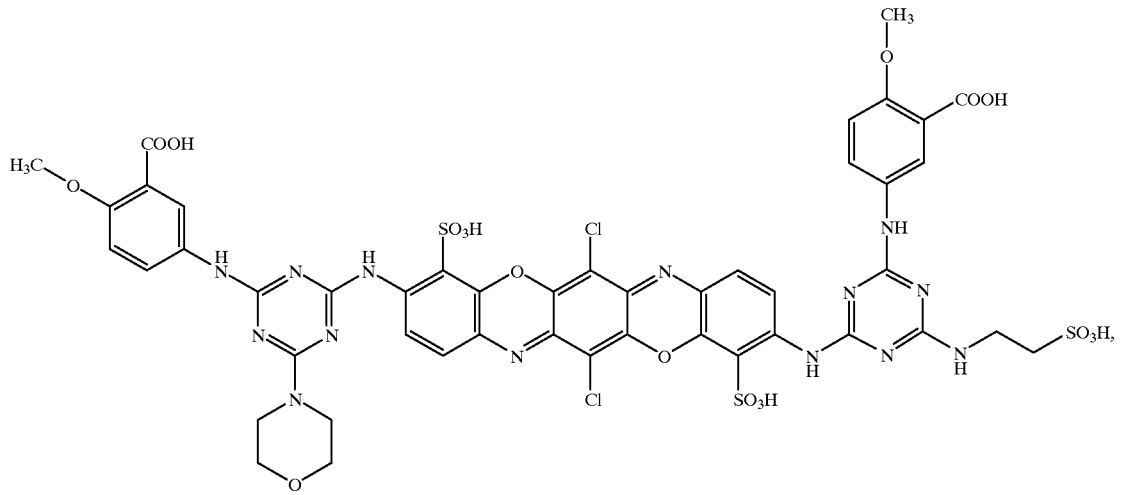
(g)
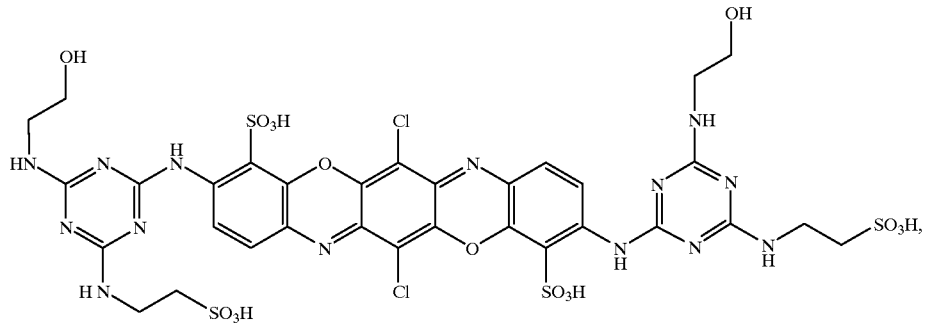
(h)

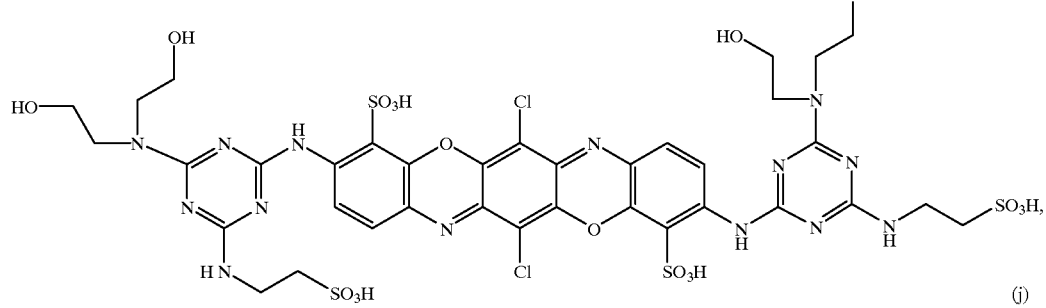
(i)
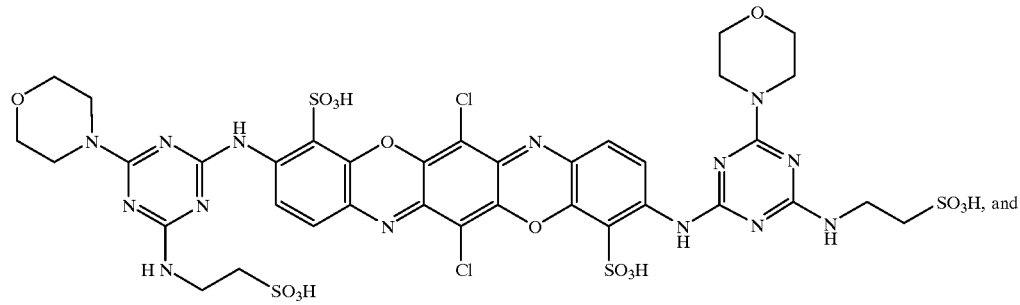
(j)
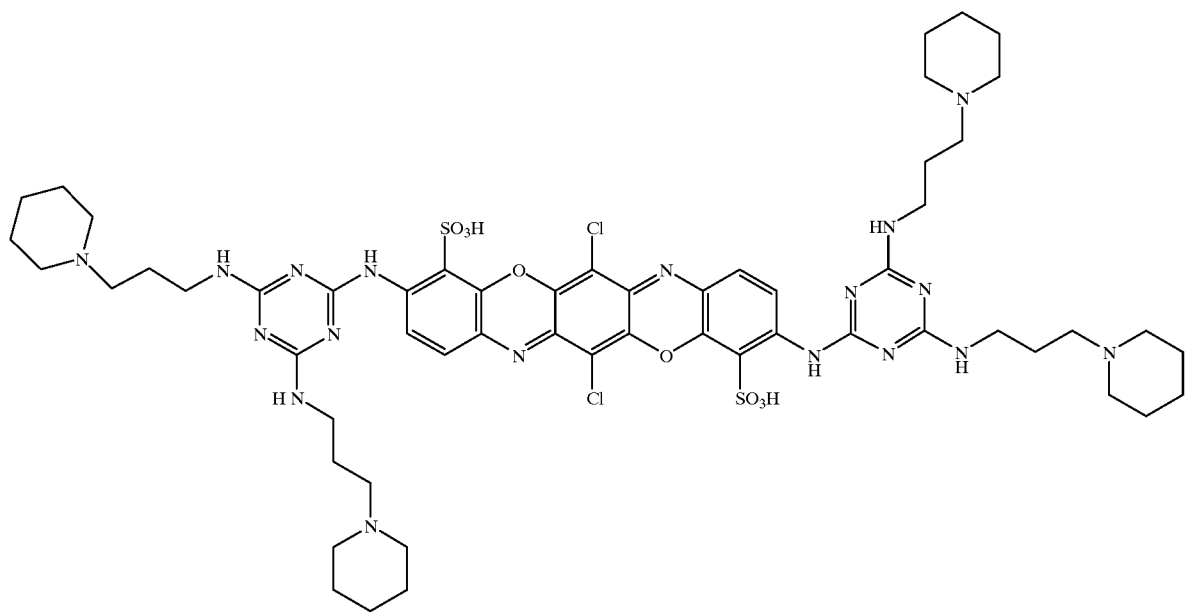
(k)
and salts thereof as well as mixture of such compounds.
4. A process for producing compounds of formula (I)
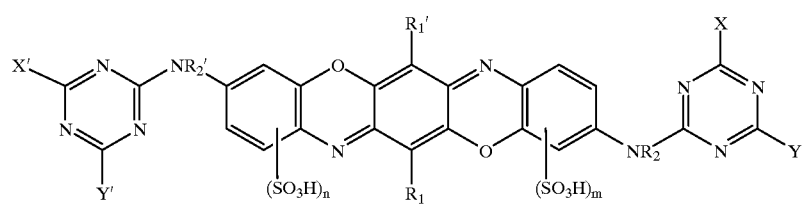
(I)
wherein X, X', $R_1$, $R_1'$, $R_2$, $R_2'$, Y, Y', m and n are the same as in claim 1 and formulae (a)–(k) according to claim 3 where a compoung of formula (II)

(II)

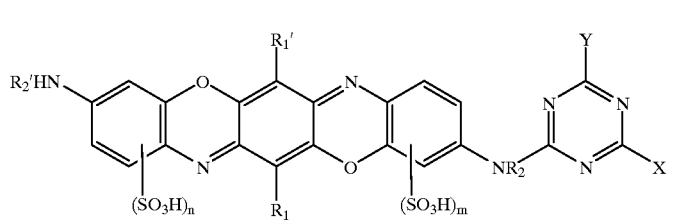

with the meanings of the symbols as defined in claim 1 is reduced to the corresponding leuco form (IIa)

(IIa)

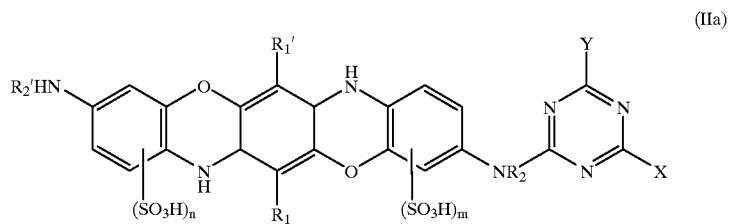

with the same meanings of the substituents as defined in claim 1, which is then reacted with one mole of the compound of formula (III)

(III)

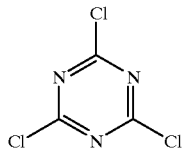

and the remaining chlorine atoms of the triazine ring are replaced by X' and Y' by condensation and the compound is oxidized to a compound according to formula (I).

5. A process for producing compounds of formula (I)

(I)

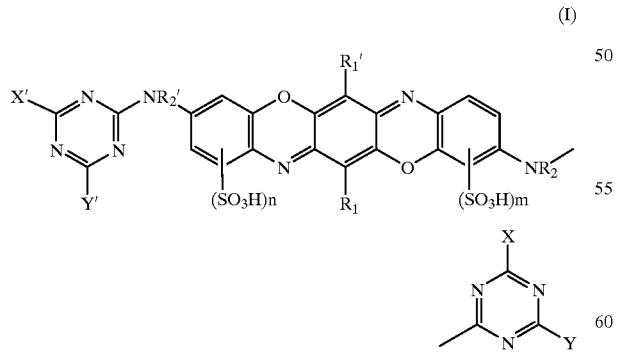

wherein X, X', $R_1$, $R_1'$, $R_2$, $R_2'$, Y, Y', m and n are the same as in claim 1 and formulae (a)–(k) according to claim 3 characterized in that a compound of formula (IV)

(IV)

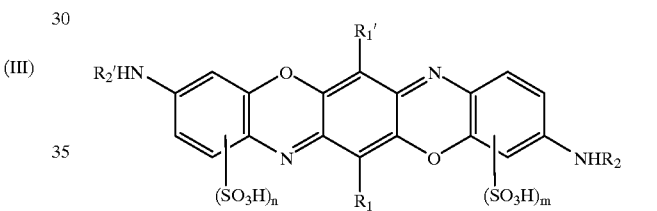

with the same meaning for $R_1$, $R_1'$, $R_2$, $R_2'$, m and n as defined in claim 1 is reduced to the corresponding leuco form (V)

(V)

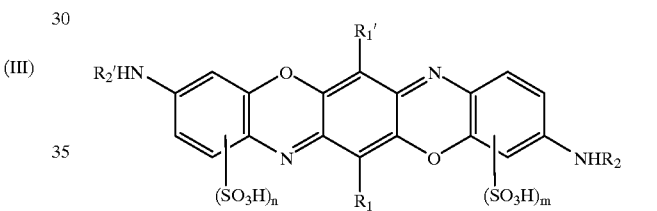

with the same definitions for substituents as defined in claim 1 and two moles a compound of formula (III)

(III)

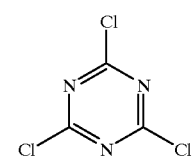

react with the compound of formula (V); two moles of a compound HX or HX' and two moles of a compound HY or HY' are condensed to the triazine rings of triphendioxazine backbone and the compound is oxidized.

6. A process according to claim 4 where a mono-and/or di-substituted cyanuric chloride compounds according to formula (IIIa) respectively according to formula (IIIb)

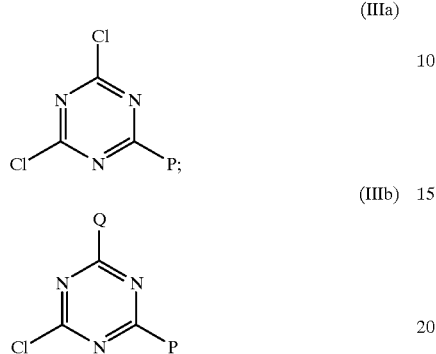

wherein P and Q signify X, X', Y and Y' as defined in claim 1, are condensed to the triphendioxazine backbone according to formula (IIa)

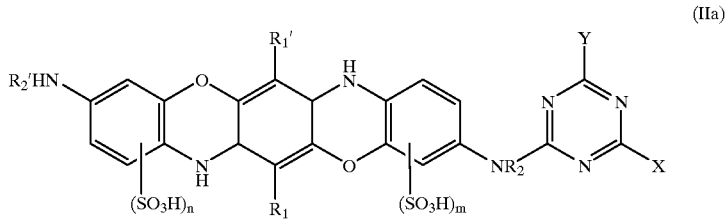

with the same meanings for the substituents as defined above, respectively according to formula (V).

7. A method for dyeing or printing organic substrates containing hydroxy groups, thiol groups or nitrogen, comprising the steps of:
    providing an organic substrates containing hydroxy groups, thiol groups or nitrogen;
    providing a dye or printing paste which contains a compound of formula (I) or mixtures thereof according to claim 1, ;and
    contacting said dye or printing paste with said organic substrates.

8. Process for dyeing or printing organic substrates containing hydroxy groups, thiol groups or nitrogen atoms, comprising the steps of:
    providing an organic substrates containing hydroxy groups, thiol groups or nitrogen;
    providing a dye or printing paste which contains a compound of formula (I) or mixtures thereof according to claim 1; and
    applying said dye or printing paste to said organic substrates.

9. Process for dyeing or printing cellulosic textile materials or paper, comprising the steps of:
    providing an organic substrates containing hydroxy groups, thiol groups or nitrogen;
    providing a dye or printing paste which contains a compound of formula (I) or mixtures thereof according to claim 1; and
    applying said dye or printing paste to said organic substrates.

10. Organic substrates dyed or printed by the process of claim 8.

11. A process for printing on paper, comprising the steps of:
    providing paper;
    providing an ink jet ink which contains a compound of formula (I) or mixtures thereof according to claim 1; and
    contacting said ink with said paper.

12. Process for the preparation of inkjet inks, comprising the steps of:
    providing a mixture of a solvent and water; and
    adding a compound of formula (I) or mixtures thereof according to claim 1 to produce an ink-jet ink.

13. Process for the preparation of ink-jet inks, comprising the steps of:
    providing a mixture of a solvent and water; and
    adding a compound of formulae (a)–(k) or mixtures thereof according to claim 3 to produce an ink-jet ink.

14. Ink-jet inks prepared by the process of claim 12.

* * * * *